United States Patent [19]

Niwa et al.

[11] Patent Number: 4,495,373

[45] Date of Patent: Jan. 22, 1985

[54] METHOD FOR PARTIAL NUCLEAR HYDROGENATION OF AROMATIC HYDROCARBON COMPOUNDS AND A HYDROGENATION CATALYST THEREFOR

[75] Inventors: Shuichi Niwa, Ibaraki; Juichi Imamura, Chofu; Fujio Mizukami, Ibaraki; Kazuo Shimizu, Ibaraki; Yoshio Orito, Ibaraki, all of Japan

[73] Assignee: Director-General of the Agency of Industrial Science and Technology, Tokyo, Japan

[21] Appl. No.: 582,565

[22] Filed: Feb. 22, 1984

[51] Int. Cl.³ ............................ C07C 5/02; C07C 5/11
[52] U.S. Cl. ..................... 585/269; 585/272; 585/273; 208/144; 502/261
[58] Field of Search ............... 502/261; 585/269, 272, 585/273; 208/144

[56] References Cited

U.S. PATENT DOCUMENTS

| | | | |
|---|---|---|---|
| 2,083,824 | 6/1937 | Bond et al. | 502/261 |
| 3,432,565 | 3/1969 | Kouwenhoven et al. | 585/269 |
| 3,491,019 | 1/1970 | Pollitzer et al. | 585/269 |
| 3,531,536 | 9/1970 | Gerhold | 585/269 |
| 3,637,879 | 1/1972 | Hayes | 585/269 |
| 3,700,742 | 10/1972 | Hayes | 585/269 |
| 3,912,787 | 10/1975 | Nowack et al. | 585/272 |
| 4,051,017 | 9/1977 | Beaty, Jr. | 208/135 |
| 4,097,412 | 6/1978 | Muller | 502/332 |
| 4,197,415 | 4/1980 | Hideyuki et al. | 585/269 |
| 4,212,990 | 7/1980 | Yasuhara et al. | 585/269 |
| 4,225,733 | 9/1980 | Kameyama et al. | 585/269 |

FOREIGN PATENT DOCUMENTS 58-48305  5/1983  Japan ................... 585/269

OTHER PUBLICATIONS

Blanchard et al., "Hydrocarbon Conversion Reactions over Platinum-Ruthenium Alloys Supported Catalysts", Nouveau Journal de Chimie, vol. 5, Feb. 1981, pp. 85–89, (Translation).

*Primary Examiner*—Delbert E. Gantz
*Assistant Examiner*—Lance Johnson
*Attorney, Agent, or Firm*—Brisebois & Kruger

[57] ABSTRACT

The invention provides an improvement in the partial nuclear hydrogenation of an aromatic hydrocarbon compound in the liquid phase with admixture of water catalyzed by a ruthenium-containing solid catalyst. The scope of the invention is in the use of a novel ruthenium-containing catalyst supported on a silica gel and the like carrier and the catalyst is prepared by the hydrolysis and gelation of an alkoxide of silicon or aluminum in a solution containing a ruthenium compound, e.g. ruthenium alkoxide, followed by drying of the gelled material so that the resultant catalyst is very uniformly impregnated with the ruthenium ingredient to be imparted with greatly improved catalytis activity and selectivity for the intended reaction over conventional ruthenium-containing catalysts prepared by post-impregnation of a preformed silica gel carrier.

17 Claims, No Drawings ton compound in a liquid phase promoted by a hydrogenation catalyst or, more particularly, to a method for the preparation of a cyclic olefin compound by the partial hydrogenation of an aromatic hydrocarbon compound in a liquid phase promoted by a solid catalyst and a novel ruthenium-containing catalyst therefor.

METHOD FOR PARTIAL NUCLEAR HYDROGENATION OF AROMATIC HYDROCARBON COMPOUNDS AND A HYDROGENATION CATALYST THEREFOR

BACKGROUND OF THE INVENTION

The present invention relates to a method for the partial nuclear hydrogenation of an aromatic hydrocarbon compound in a liquid phase promoted by a hydrogenation catalyst or, more particularly, to a method for the preparation of a cyclic olefin compound by the partial hydrogenation of an aromatic hydrocarbon compound in a liquid phase promoted by a solid catalyst and a novel ruthenium-containing catalyst therefor.

As is well known, partial nuclear hydrogenation products of aromatic hydrocarbon compounds, such as cyclohexene, alkyl cyclohexenes and the like, are useful compounds as an important intermediate in the synthesis of various kinds of organic compounds so that it has been eagerly desired to develop a novel and efficient industrial method for the synthetic preparation of these compounds. The conventional hydrogenation method of an aromatic hydrocarbon compound, however, involves a rather difficult problem when preparation of a partial nuclear hydrogenation product is intended by the method because the hydrogenation reaction can hardly be limited at the intermediate stage of the partial hydrogenation of the aromatic nucleus which is usually hydrogenated completely to give a cycloparaffin compound.

Several methods have been proposed already for the partial hydrogenation of the aromatic nuclei. For example, West German Patents No. 1,443,377 and No. 1,793,757 teach a method of hydrogenation in a medium of liquid ammonia in the presence of an alkali metal. Although this method can give a relatively high yield of the desired partial hydrogenation product, the method is not always advantageous for the industrial production of the products due to the complicated process for performing the reaction.

An alternative method with some industrial feasibility has been proposed, for example, in Japanese Patent Kokai Nos. 53-46938, 53-65849 and 53-63350 in which the hydrogenation of an aromatic hydrocarbon compound is carried out in the presence of water by use of a ruthenium catalyst. The ruthenium catalyst disclosed in these patents is a solid ruthenium catalyst supported on a porous carrier such as silica, alumina and the like. The yield of the desired partial hydrogenation product is, however, relatively low in this method so that this method also has a low industrial value.

Recently, an improved method for the partial nuclear hydrogenation of an aromatic hydrocarbon compound is disclosed in Japanese Patent Kokai No. 57-130926 according to which a considerably large amount of cobalt sulfate is added to the reaction mixture containing a solid ruthenium-containing catalyst prepared by impregnating a carrier such as silica, alumina and the like with ruthenium chloride followed by activation by reduction with hydrogen. This method is seemingly promising to some extent with a relatively high yield of the desired product but a very serious problem encountered in practicing this method is the corrosion of the material of the reaction vessel which should withstand the very severe reaction conditions of the use of a large amount of cobalt sulfate in the presence of water at a high reaction temperature of, for example, 170° C.

Thus, it has been generally accepted that the use of a ruthenium-containing solid catalyst supported on a carrier of silica, alumina and the like is not practically feasible for the purpose and there is an eager demand for the development of a novel and efficient method for the partial nuclear hydrogenation of an aromatic hydrocarbon compound.

Thus, no satisfactory method is known from the standpoint of industrial production for the preparation of a partially nuclear-hydrogenated product of an aromatic hydrocarbon compound.

SUMMARY OF THE INVENTION

It is therefore an object of the present invention to provide a novel and efficient method for the industrial preparation of a partially nuclear-hydrogenated product of an aromatic hydrocarbon compound by a catalytic hydrogenation reaction in the liquid phase free from the above described problems and disadvantages in the prior art methods.

Another object of the present invention is to provide an improvement in a catalytic hydrogenation reaction of an aromatic hydrocarbon compound to produce a partially nuclear-hydrogenated product by use of a ruthenium catalyst supported on a carrier such as silica gel, alumina gel and the like.

A further object of the invention is to provide a ruthenium-containing solid catalyst having high activity and selectivity in the partial nuclear hydrogenation of an aromatic hydrocarbon compound in a liquid phase catalytic reaction as well as a method for the preparation of such a ruthenium catalyst.

The method of the present invention for the preparation of a partially nuclear-hydrogenated product of an aromatic hydrocarbon compound comprises reacting an aromatic hydrocarbon compound admixed with water in the liquid phase with hydrogen in the presence of a solid ruthenium catalyst supported on a carrier of silica, alumina or silica-alumina gel, said ruthenium catalyst being prepared by the hydrolysis and gelation of an alkoxide of silicon or aluminum in the presence of a ruthenium compound to give a ruthenium-containing gel of silica or alumina followed by drying and activation thereof.

It is further noted that the performance of the above described ruthenium catalyst prepared by a specific method can be enhanced when the catalyst contains copper uniformly distributed therein as a cocatalytic ingredient.

It is also noted that the efficiency of the partial nuclear hydrogenation reaction is increased when the reaction mixture contains an ester of phosphoric acid as a reaction promotor.

DETAILED DESCRIPTION OF THE PREFERRED EMBODIMENTS

The aromatic hydrocarbon compound as the starting reactant to be partially hydrogenated on the aromatic nucleus is exemplified by monocyclic aromatic hydrocarbon compounds including benzene, toluene, xylene, ethylbenzene, cumene, mesitylene and other alkylbenzenes. The efficiency of the inventive method is remarkably high when the starting aromatic hydrocarbon compound is a monocyclic aromatic hydrocarbon compound or, in particular, benzene or an alkylbenzene although the method is also applicable to polycyclic aromatic phydrocarbon compounds. The application of the inventive method to the partial nuclear hydrogenation of benzene or an alkylbenzene is of larger industrial significance due to the usefulness of the products derived from these starting reactants.

As is understood from the above given description of the SUMMARY OF THE INVENTION, the most characteristic feature in the inventive method is in the use of a very specific ruthenium catalyst supported on a silica or alumina gel as the carrier. The ruthenium-containing hydrogenation catalyst used in the inventive method is prepared by the hydrolysis of an alkoxide of silicon or aluminum or a mixture of them in an medium containing a ruthenium compound dissolved therein followed by the gelation to form a ruthenium-containing gel of silica and/or alumina which is then dried and activated prior to use in the hydrogenation reaction.

The alkoxide of silicon or aluminum used as the starting material of the carrier gel of the ruthenium catalyst is readily prepared by the reaction of a halide, e.g. chloride, of the respective element with an alcohol such as methyl alcohol, ethyl alcohol, isopropyl alcohol, ethyleneglycol and the like.

The ruthenium catalyst used in the inventive method is prepared by utilizing the phenomenon of gelation of the hydrolyzate formed by the hydrolysis of the above mentioned alkoxide of silicon and/or aluminum. For example, the alkoxide and a suitable ruthenium compound are dissolved together in an organic solvent and the solution is heated under agitation with admixture of a small amount of water. The alkoxide is then hydrolyzed and the dehydration condensation of the hydrolyzate takes place concurrently to gradually form a gelled material containing the ruthenium compound therein. Drying of the thus formed gelled material with heating gives a silica or alumina gel uniformly impregnated with the ruthenium compound.

The ruthenium compound which should be soluble in an organic solvent together with the alkoxide of silicon or aluminum is exemplified by the salts or ruthenium, e.g. halides, such as ruthenium chloride, ruthenium bromide and the like, and ruthenium acetylacetonate as well as various kinds of complexes of ruthenium including ruthenium ammine complexes with a chelating agent such as ethylene diamine, phenanthroline, bipyridyl and the like, carbonyl ruthenium complexes and ruthenocene and the like organic complexes of ruthenium and ruthenium alkoxides. Ruthenium alkoxides are particularly preferable in respect of the outstandingly high yield of the desired products when the catalyst prepared therefrom is used in the reaction.

The solvent in which the hydrolysis of the alkoxide of silicon or aluminum should preferably be a polar organic solvent from the standpoint of the solubility of both of the alkoxide and the ruthenium compound including monohydric alcohols such as methyl and ethyl alcohols, polyhydric alcohols such as ethyleneglycol, propyleneglycol and glycerin and acethylacetone. When an alcoholic solvent is used, an advantage is obtained in that an alkoxide of ruthenium is formed in situ from a ruthenium compound other than alkoxide and the ruthenium alkoxide is cohydrolyzed with the alkoxide of silicon or aluminum in the alcoholic solution. Particularly preferable alcoholic solvents are the monohydric alcohols having a relatively high boiling point and lower polyols having, for example, 2 to 4 carbon atoms in a molecule, among which ethyleneglycol and propyleneglycol are the most preferable from the practical standpoint.

The hydrolysis reaction of the alkoxide of silicon or aluminum in an organic solution containing a ruthenium compound usually takes a relatively long time of 2 to 40 hours but the reaction can be greatly accelerated by the addition of a catalytic amount, say, from 0.01 to 1% by weight of the alkoxide, of a catalyst for the reaction of hydrolysis so that the reaction may be complete within several minutes. Particularly preferable hydrolysis catalysts are certain organic acids such as formic acid, tartaric acid, citric acid and the like. These organic acids are effective even in a trace amount of addition and the performance of the resultant ruthenium catalyst is little affected by the addition of these organic acids as the hydrolysis catalyst. It should be noted, however, that the use of a hydrolysis catalyst, such as propylene diamine and potassium sodium tartrate, may adversely affect the performance of the resultant ruthenium catalyst to a great extent. Therefore, the hydrolysis of the alkoxide should be performed without addition of any catalyst for safety reason in view of the fact that no improvement can be expected at any rate in the performance of the resultant ruthenium catalyst.

The performance of the ruthenium catalyst of the invention supported on silica, alumina or silica-alumina gel and prepared from the alkoxide by the hydrolysis in the presence of a ruthenium compound is surprisingly much better than that of the conventional ruthenium catalysts on silica or alumina gel prepared by the post-impregnation of a preformed gel with a ruthenium compound. Among the types of the gels supporting the ruthenium ingredient in the inventive ruthenium catalyst, silica gel is preferable to alumina and silica-alumina gels. As is shown later by the examples, for example, the yield of cyclohexene from benzene by use of the silica-supported ruthenium catalyst of the invention is more than two times larger than with an alumina-supported ruthenium catalyst containing the same amount of the ruthenium ingredient although the value of yield obtained by use of the alumina-supported ruthenium catalyst of the invention is still more than two times larger than that obtained with a conventional alumina-supported ruthenium catalyst of the same ruthenium content.

The content of the ruthenium ingredient in the silica- or alumina-supported catalyst of the invention should be in the range from 0.01 to 50% by weight or, preferably, from 0.1 to 5% by weight and should be determined in consideration of various factors. When the starting reactant of the aromatic hydrocarbon compound is limited to benzene or a methylbenzene, however, better results can hardly be expected even by the increase of the ruthenium content in the catalyst over 2 to 3% by weight so that the ruthenium content should be limited not to exceed this upper limit in view of the economy in relation to the use of a relatively expensive ruthenium compound.

It has been further discovered that a trace amount of copper in the ruthenium catalyst of the invention has a remarkable cocatalytic effect when the copper ingredient is added to the hydrolysis mixture for the hydrolysis of the alkoxide of silicon or aluminum in the presence of a ruthenium compound. Any copper compound soluble in the mixture may be used in this purpose including, for example, halides, e.g. chlorides, of copper. The amount of addition of the copper compound should be in the range from 1 to 30% by weight or, preferably, from 2 to 20% by weight based on the ruthenium content each calculated on the metal base. The cocatalytic effect of copper in the inventive ruthenium catalyst is very specific to copper and no such an effect can be expected with other metals excepting silver which is somewhat effective though much less remarkably than copper or rather many of other metals including iron and renium have an adverse effect to the contrary.

The ruthenium catalyst of the invention prepared by the hydrolysis and gelation of an alkoxide of silicon or aluminum followed by drying should be activated before use by a conventional technique of reduction in a stream of hydrogen gas. This treatment of reduction is performed by passing a stream of hydrogen in a reactor tube containing the catalyst at a rate of 0.05 to 50 liters per hour or, preferably, 0.5 to 10 liters per hour per 1 g of the catalyst for 10 minutes to 100 hours or, preferably, 30 minutes to 20 hours at a temperature of 50 to 900° C. or, preferably, 200° to 600° C. The thus activated catalyst of the invention is now ready for use in the hydrogenation reaction of the aromatic hydrocarbon compound.

The reaction of the partial nuclear hydrogenation of the aromatic hydrocarbon compound in the invention is performed by heating the hydrocarbon compound admixed with water in the presence of the above described ruthenium catalyst of the invention under an atmosphere of hydrogen. The amounts of water and the ruthenium catalyst should be in the range from 1 to 20000 parts by weight or, preferably, from 10 to 500 parts by weight and from 0.01 to 50 parts by weight or, preferably, from 0.1 to 10 parts by weight, respectively, per 100 parts by weight of the starting aromatic hydrocarbon compound. The temperature of the reaction mixture should be in the range from 50° to 300° C. or, preferably, from 100° to 220° C. and the pressure should be in the range from atmospheric pressure to 500 kg/cm$^2$G. The reaction time was preferably in the range from 0.5 to 5 hours but the reaction is usually complete within 1 hour and extension of the reaction time has no particular effect for the improvement in the yield of the desired product.

It has been also discovered that the reaction according to the inventive method can be promoted by the addition of a small amount of an ester of phosphoric acid to the reaction mixture to give a higher yield of the desired product. The phosphoric acid ester is preferably an diester or triester. The alcoholic constituent forming an ester with phosphoric acid is not particularly limitative but it is preferably a monohydric aliphatic alcohol having at least 4 carbon atoms in a molecule or a monoalkyl ether of a glycol compound represented by the general formula $R \!\!-\!\!(O\!-\!CH_2\!-\!CH_2)_n\!OH$, in which R is an alkyl group having 10 to 14 carbon atoms and n is 1 or 2. The amount of the phosphoric acid ester to be added to the reaction mixture should be, though dependent on various factors such as the kind of the starting aromatic hydrocarbon compound and the amount of water in the reaction mixture, in the range from 0.01 to 3% by weight or, preferably, from 0.1 to 1.5% by weight based on the amount of the aromatic hydrocarbon compound as the starting reactant. It should be noted that addition of an excessively large amount of a phosphoric acid ester is undesirable due to the possible adverse effects to a large extent so that the optimum amount of the phosphoric acid ester should be carefully determined by preliminary experimentation in consideration of the kind of the starting reactant, amount of water, reaction temperature, amount of the catalyst and other factors.

The hydrogenation reaction according to the inventive method can be performed either batch-wise or as a continuous process. It is optional that the starting aromatic hydrocarbon compound is diluted with a suitable inert solvent such as hexane although no particular advantages are obtained by the use of a solvent when the starting aromatic hydrocarbon compound is liquid at the reaction temperature so that the reaction is carried out usually without solvent.

In the following, preparation of the inventive ruthenium catalyst and the method of the partial nuclear hydrogenation of an aromatic hydrocarbon compound according to the inventive method are described in detail by way of examples. In the following examples, the organic layer of the reaction mixture after completion of the reaction was analyzed by gas chromatography to calculate the value of reactant conversion in %, which is a ratio of the decreased amount of the aromatic hydrocarbon compound to the initial amount of the compound taken in the reaction mixture, and the value of selectivity in % which is a ratio of the desired product produced in the reaction mixture after the reaction to the decreased amount of the aromatic hydrocarbon compound in the molar basis. Thus, the yield of the desired product is given by multiplying the reactant conversion with the selectivity.

EXAMPLE 1

Into a flask of 500 ml capacity were introduced 1.0 g of ruthenium chloride $RuCl_3$ and 100 ml of ethyleneglycol and the mixture was heated for 2 hours at 60° C. under agitation. Thereafter, the mixture was further admixed with 132.5 g of orthoethyl silicate $Si(OC_2H_5)_4$ and heated at 60° C. for additional 2 hours under agitation followed by the addition of 100 ml of water and further heating at 60° C. for 8 hours. A dark green, gelled material was formed in the reaction mixture during this treatment. This gelled material was taken out and dried under reduced pressure at 80° C. in an evaporator to give a granular product which was ground in a mortar into about 40 g of a fine powder. The thus obtained catalyst contained about 1% by weight of ruthenium ingredient supported on silica gel.

EXAMPLE 2

The same experimental procedure as in Example 1 was repeated except that the amount of the ruthenium chloride was increased to 2.0 g. The resultant silica-supported ruthenium catalyst contained about 2% of the ruthenium ingredient.

EXAMPLE 3

The same experimental procedure as in Example 1 was repeated except that the amount of the ruthenium chloride was increased to 2.0 g and 0.2 g of copper (II) chloride was additionally added to the reaction mixture. The resultant silica-supported catalyst contained about 2% by weight of ruthenium and about 0.2% by weight of copper.

EXAMPLE 4

Into a flask of 500 ml capacity were taken 2.0 g of ruthenium chloride $RuCl_3$ and 100 ml of ethyleneglycol and the mixture was heated at 60° C. for 2 hours under agitation. Thereafter, 78 g of aluminum isopropoxide dissolved in 100 ml of isopropyl alcohol were added to the above mixture followed by further agitation at 60° C. for 2 hours. Addition of water to effect hydrolysis followed by gelation was performed in the same manner as in Example 1 to obtain an alumina gel containing about 2% by weight of the ruthenium ingredient.

EXAMPLE 5

Into a flask of 500 ml capacity were taken 2.0 g of ruthenium chloride $RuCl_3$ and 100 ml of ethyleneglycol and the mixture was heated at 60° C. for 2 hours under agitation followed by the addition of 132.5 g of orthoethyl silicate with further agitation of the mixture at 60° C. for additional 2 hours. Thereafter, 5 g of tartaric acid dissolved in 100 ml of water were added to the mixture which was agitated for 10 minutes at 60° C. to form a gelled material therein. This gelled material was processed in the same manner as in Example 1 to give a silica gel containing about 2% of the ruthenium ingredient.

EXAMPLE 6

The activation of the ruthenium catalyst was performed by heating and reducing 2 g of the silica-supported ruthenium catalyst prepared in Example 2 above at 400° C. for 8 hours under a stream of hydrogen gas flowing at a rate of 6 liters per hour.

Into an autoclave of 500 ml capacity were introduced 160 ml of benzene, 50 ml of water and 2 g of the ruthenium catalyst activated in the above described manner and the autoclave was closed after complete replacement of the air inside with hydrogen. Then, the temperature of the reaction mixture was increased up to 180° C. under a hydrogen pressure kept at 70 kg/cm$^2$G while the electromagnetic stirrer of the autoclave was driven at a velocity of 800 r.p.m. Gas chromatographic analysis of a small portion of the reaction mixture periodically taken out of the autoclave indicated that the reactant conversion of benzene after 1 hour of the reaction time was 68.32% and the selectivity for the formation of cyclohexene was 39.47% by moles to give a yield of cyclohexene of 27.0%.

For comparison, the same experimental procedure as above was repeated except that the inventive ruthenium catalyst was replaced with the same amount of a conventional silica-supported ruthenium catalyst containing 2% by weight of the ruthenium ingredient. The results were that the yield of cyclohexene after 1 hour of the hydrogenation reaction was only 8.6%.

EXAMPLE 7

The same experimental procedure as in Example 6 was repeated except that the ruthenium catalyst prepared in Example 1 and containing 1% by weight of the ruthenium ingredient was used in place of the catalyst of Example 2. The results were that the reactant conversion of benzene was 66.6% after 1 hour of the reaction with 37.98% by moles of selectivity for the formation of cyclohexene to give a yield of 25.3%.

EXAMPLE 8

The same experimental procedure as in Example 6 was repeated except that the amount of the ruthenium catalyst was increased to 3.0 g. The results after 1 hour of the reaction were that the reactant conversion of benzene was 68.1% and the selectivity for the formation of cyclohexene was 40.45% by moles to give a yield of 27.5%.

EXAMPLE 9

The same experimental procedure as in Example 6 was repeated except that the ruthenium catalyst prepared in Example 2 was replaced with the same amount of the copper-containing ruthenium catalyst prepared in Example 3. The results after 1 hour of the reaction were that the conversion of benzene was 67.5% and the selectivity for the formation of cyclohexene was 38.6% by moles to give a yield of 29.5%.

EXAMPLE 10

The same experimental procedure as in Example 9 was repeated except that the aromatic hydrocarbon compound was toluene instead of benzene. The results after 1 hour of the reaction were that the conversion of toluene was 63.3% and the selectivity for the formation of methyl cyclohexene was 55.9% by moles to give a yield of 35.4%.

EXAMPLE 11

The same experimental procedure as in Example 9 was repeated except that the aromatic hydrocarbon compound was o-xylene instead of benzene. The results after 1 hour of the reaction were that the conversion of the o-xylene was 76.3% and the selectivity for the formation of dimethyl cyclohexene was 50.5% by moles to give a yield of 38.5%.

EXAMPLE 12

The reaction conditions were the same as in Example 9 excepting the further addition of 0.6 ml of di(2-ethylhexyl) phosphate or trioctyl phosphate to the reaction mixture. The results after 1 hour of the reaction were that the conversion of benzene was 78.7% and the selectivity for the formation of cyclohexene was 38.2% by moles to give a yield of 30.1% when di(2-ethylhexyl) phosphate was added and the conversion of benzene was 78.0% and the selectivity for the formation of cyclohexene was 41.8% to give a yield of 32.6% when trioctyl phosphate was added.

EXAMPLE 13

The same experimental procedure as in Example 6 was repeated except that the ruthenium-containing silica gel catalyst was replaced with the same amount of the ruthenium-containing alumina gel catalyst prepared in Example 4. The yield of the cyclohexene after 1 hour of the reaction was 11.5%.

For comparison, the same experiment was repeated but by use of a ruthenium-containing alumina gel catalyst obtained on the market. In this case, the yield of the cyclohexene was only 5.4% at the highest.

EXAMPLE 14

The same experimental procedure as in Example 6 was repeated excepting the use of the ruthenium-containing silica gel catalyst prepared in Example 5. The results obtained after 1 hour of the reaction were that the conversion of benzene was 75.9% and the selectivity was 35.0% by moles to give a yield of 26.5% at the highest.

What is claimed is:

1. A method for the preparation of a partially nuclear-hydrogenated product of an aromatic hydrocarbon compound which comprises reacting the aromatic hydrocarbon compound in the liquid phase admixed with water with hydrogen in the presence of a ruthenium-containing solid catalyst with silica, alumina or silica-alumina gel as the carrier, said ruthenium-containing solid catalyst being produced by subjecting a silicon alkoxide, aluminum alkoxide or a mixture thereof to hydrolysis and gelation in the presence of a ruthenium compound to form a gel of silica, alumina or silica-alumina as the carrier uniformly impregnated with ruthenium followed by drying.

2. The method as claimed in claim 1 wherein the carrier of the ruthenium-containing solid catalyst is silica.

3. The method as claimed in claim 1 wherein the ruthenium-containing solid catalyst contains from 0.1 to 5% by weight of ruthenium.

4. The method as claimed in claim 1 wherein the ruthenium-containing solid catalyst further contains copper as a cocatalyst.

5. The method as claimed in claim 4 wherein the ruthenium-containing solid catalyst contains from 2 to 20% by weight of copper based on the content of ruthenium.

6. The method as claimed in claim 1 wherein the amount of water is in the range from one tenth to 5 times by weight of the aromatic hydrocarbon compound.

7. The method as claimed in claim 1 wherein the amount of the ruthenium-containing solid catalyst is in the range from 0.1 to 10% by weight based on the amount of the aromatic hydrocarbon compound.

8. The method as claimed in claim 1 wherein the reaction of the aromatic hydrocarbon compound with hydrogen is performed at a temperature in the range from 100° to 220° C.

9. The method as claimed in claim 1 wherein the reaction of the aromatic hydrocarbon compound with hydrogen is performed in an atmosphere of hydrogen under a pressure in the range from 10 to 200 kg/cm$^2$G.

10. The method as claimed in claim 1 wherein the ruthenium-containing solid catalyst is activated prior to the reaction by reducing with hydrogen at a temperature in the range from 200° to 600° C.

11. The method as claimed in claim 1 wherein the aromatic hydrocarbon compound is further admixed with an ester of phosphoric acid as a reaction promotor.

12. The method as claimed in claim 11 wherein the ester of phosphoric acid is a diester or triester of phosphoric acid with an alcohol selected from the class consisting of aliphatic monohydric alcohols having at least 4 carbon atoms in a molecule and monoalkyl ethers of a glycol compound represented by the general formula R—O—CH$_2$CH$_2$)$_n$OH, in which R is an alkyl group having 10 to 14 carbon atoms and n is 1 or 2.

13. The method as claimed in claim 12 wherein the alcohol is octyl alcohol.

14. The method as claimed in claim 11 wherein the amount of the ester of phosphoric acid is in the range from 0.1 to 1.5% by weight based on the amount of the aromatic hydrocarbon compound.

15. The method of claim 1 wherein the ruthenium compound from which the solid catalyst is provided is an alkoxide of ruthenium.

16. The method of claim 15 wherein the alkoxide of ruthenium is formed as a solution of ruthenium alkoxide in an alcoholic solution by the reaction of a ruthenium compound with an alcohol and the hydrolysis and gelation of the silicon alkoxide, aluminum alkoxide or a mixture thereof is performed by the addition thereof to the alcoholic solution of the ruthenium alkoxide.

17. The method of claim 16 wherein the alcohol is ethyleneglycol.

* * * * *

UNITED STATES PATENT AND TRADEMARK OFFICE
CERTIFICATE OF CORRECTION

PATENT NO.   :   4,495,373

DATED        :   January 22, 1985

INVENTOR(S)  :   Shuichi NIWA et al.

It is certified that error appears in the above-identified patent and that said Letters Patent is hereby corrected as shown below:

On the title page:
In the heading insert:

[30]   Foreign Priority Data:

[32]   Priority February 24, 1983
         [33]   Japan
         [31]   58-29856

Signed and Sealed this

Eleventh Day of June 1985

[SEAL]

Attest:

DONALD J. QUIGG

*Attesting Officer*    *Acting Commissioner of Patents and Trademarks*